(12) United States Patent
Kim et al.

(10) Patent No.: US 11,396,605 B2
(45) Date of Patent: Jul. 26, 2022

(54) HEAT EXCHANGER

(71) Applicant: LG ELECTRONICS INC., Seoul (KR)

(72) Inventors: Jihyun Kim, Seoul (KR); Donghan Kim, Seoul (KR); Chohee Oh, Seoul (KR); Seojin Lee, Seoul (KR); Taegyu Jin, Seoul (KR); Sanghyun Hong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 124 days.

(21) Appl. No.: 16/631,931

(22) PCT Filed: Jul. 12, 2018

(86) PCT No.: PCT/KR2018/007906
§ 371 (c)(1),
(2) Date: Jan. 17, 2020

(87) PCT Pub. No.: WO2019/017647
PCT Pub. Date: Jan. 24, 2019

(65) Prior Publication Data
US 2020/0157359 A1     May 21, 2020

(30) Foreign Application Priority Data
Jul. 19, 2017 (KR) .................. 10-2017-0091672

(51) Int. Cl.
*C09D 5/08* (2006.01)
*A61L 2/232* (2006.01)
(Continued)

(52) U.S. Cl.
CPC .............. *C09D 5/084* (2013.01); *A61L 2/232* (2013.01); *A61L 9/01* (2013.01); *C09D 129/04* (2013.01);
(Continued)

(58) Field of Classification Search
CPC .......... A61L 2/232; A61L 9/01; C09D 5/084; C09D 129/04; C09D 133/02;
(Continued)

(56) References Cited

U.S. PATENT DOCUMENTS 6,013,372 A   1/2000 Hayakawa et al.
6,337,129 B1   1/2002 Watanabe et al.
(Continued)

FOREIGN PATENT DOCUMENTS

CN       1776345       5/2006
CN     104411167       3/2015
(Continued)

OTHER PUBLICATIONS

International Search Report dated Oct. 12, 2018 issued in Application No. PCT/KR2018/007906.
(Continued)

*Primary Examiner* — Eric S Ruppert
*Assistant Examiner* — Hans R Weiland
(74) *Attorney, Agent, or Firm* — KED & Associates LLP

(57) ABSTRACT

A heat exchanger is provided that is operated in a cooling operation mode in which a region to be heat-exchanged is cooled by the heat exchanger or in a drying operation mode in which the heat exchanger is supplied with wind from a blowing fan. The heat exchanger includes a refrigerant pipe, a cooling fin coupled to the refrigerant pipe, and a hydrophilic coating coated on a surface of the refrigerant pipe or the cooling fin. The hydrophilic coating includes a first type transition metal oxide which becomes acidic by reacting with moisture formed on the refrigerant pipe or the cooling fin to have antimicrobial activity when the heat exchanger is operated in the cooling operation mode, and a second type transition metal oxide or a post-transition metal oxide which (Continued)

US 11,396,605 B2
Page 2 has antimicrobial activity when the heat exchanger is operated in the drying operation mode.

11 Claims, 8 Drawing Sheets

(51) Int. Cl.
| | |
|---|---|
| *A61L 9/01* | (2006.01) |
| *F28F 13/18* | (2006.01) |
| *F28F 19/06* | (2006.01) |
| *C09D 129/04* | (2006.01) |
| *C09D 133/02* | (2006.01) |
| *C09D 139/06* | (2006.01) |
| *C09D 167/04* | (2006.01) |

(52) U.S. Cl.
CPC ......... *C09D 133/02* (2013.01); *C09D 139/06* (2013.01); *C09D 167/04* (2013.01); *F28F 13/182* (2013.01); *F28F 19/06* (2013.01); *F28F 2245/02* (2013.01); *F28F 2265/20* (2013.01)

(58) Field of Classification Search
CPC ... C09D 139/06; C09D 167/04; F28F 13/182; F28F 13/22; F28F 19/04; F28F 19/06; F28F 2245/00; F28F 2245/02; F28F 2265/20; F24F 2013/221
See application file for complete search history.

(56) References Cited

U.S. PATENT DOCUMENTS

| | | | | |
|---|---|---|---|---|
| 2003/0039849 | A1* | 2/2003 | Inbe | ............... C09D 129/04 428/457 |
| 2006/0196644 | A1 | 9/2006 | Boger et al. | |
| 2010/0252241 | A1* | 10/2010 | McDermott | ........... C25D 11/36 165/151 |
| 2011/0052662 | A1* | 3/2011 | Nakano | ................... A61L 2/238 424/443 |
| 2011/0180248 | A1* | 7/2011 | Yoshida | .................. F28F 19/04 165/185 |
| 2015/0013947 | A1* | 1/2015 | Matsui | .................. F28F 21/084 165/133 |

FOREIGN PATENT DOCUMENTS

| | | |
|---|---|---|
| EP | 0200546 | 9/1990 |
| JP | 2006-522303 | 9/2006 |
| JP | 2013-213282 | 10/2013 |
| KR | 10-2001-0002543 | 1/2001 |
| KR | 10-2005-0080392 | 8/2005 |
| KR | 10-2006-0117728 | 11/2006 |
| KR | 10-2014-0098244 | 8/2014 |

OTHER PUBLICATIONS

Chinese Office Action dated Jan. 4, 2021.
"Principle and Application of Environmental Oxidation/Reduction Treatment Technology"; Chief Editor, Yue Shi, Ning Li, and Yongfeng Li; Dec. 15, 2020; "Twelfth Five-year" Planning Materials for Colleges and Universities; Postgraduate Teaching Materials in Municipal and Environmental Engineering; Harbin Institute of Technology Press; 7 pages (English Summary) ; http:/ /img.duxiu.com/ n/jpgfs/book/base/13451372/488627677.
European Search Report dated Mar. 5, 2021.

* cited by examiner

HEAT EXCHANGER

CROSS-REFERENCE TO RELATED PATENT APPLICATIONS

This application is a U.S. National Stage Application under 35 U.S.C. § 371 of PCT Application No. PCT/KR2018/007906, filed Jul. 12, 2018, which claims priority to Korean Patent Application No. 10-2017-0091672, filed Jul. 19, 2017, whose entire disclosures are hereby incorporated by reference.

TECHNICAL FIELD

The present disclosure relates to a heat exchanger having an antimicrobial and odor removal functional surface.

BACKGROUND

Heat exchangers are used in various technical fields such as air conditioners and refrigerators. However, when a heat exchanger is continuously operated, moisture is formed on a surface of the heat exchanger. For example, in case where a heat exchanger is used as an indoor unit (evaporator) of an air conditioner, when the air conditioner is operated in a cooling mode, the temperature of the indoor unit becomes lower than room temperature. Accordingly, condensate is formed on a surface of the indoor unit.

Condensate formed on the surface of the heat exchanger causes bacterial growth. This is because bacteria grow easily in wet places. Furthermore, bacteria, such as mold, cause unpleasant odors. In order to solve this problem, it may be considered to immediately remove condensate formed on the surface of the heat exchanger by evaporating the condensate. However, in order to evaporate the condensate, heat must be applied to the surface of the heat exchanger. This method is unpreferable in that it consumes additional energy.

The use of antimicrobial substances to prevent the growth of bacteria may be taken into consideration. Antimicrobial substances are largely divided into organic and inorganic antimicrobial substances. The organic antimicrobial substances have a strong antimicrobial activity, but have a short duration and have a problem of safety due to organic substances. In contrast, the inorganic antimicrobial substances have a long duration and high safety, but have a weaker antimicrobial activity than the organic antimicrobial substances.

Korean Patent Publication No. 10-2014-0098244 (Aug. 7, 2014) discloses an inorganic substance causing an antimicrobial effect. The inorganic substance forms a hydrogen cation when in contact with a water-soluble medium to cause the antimicrobial effect.

However, according to the patent document, it is disclosed that the antimicrobial substance is applied to an injection-molded product such as plastic and the like, so as to be used in medical fields such as implants, articles such as switches and keyboards, or the like. While injection moldings are used in an environment with no great change such as room temperature, heat exchangers are fundamentally different from the injection moldings in that they selectively repeat operations such as cooling, heating, dehumidification, drying, and the like.

Therefore, there is a limit that the patent document is inappropriate to be applied to a heat exchanger.

Technical Problem

An aspect of the present disclosure is to propose a configuration capable of providing antimicrobial and odor removal functions at all times to a heat exchanger that selectively repeats various operations.

Another aspect of the present disclosure is to provide a heat exchanger having optimal antimicrobial and odor removal functions through detailed physical properties such as composition, size, and thickness of an antimicrobial substance.

Technical Solution

In order to achieve these and other advantages and in accordance with the purpose of this specification, as embodied and broadly described herein, there is provided a heat exchanger operated in a cooling operation mode for cooling a region to be heat-exchanged or in a drying operation mode for receiving wind supplied from a blowing fan. The heat exchanger may include a refrigerant pipe defining a flow path of a refrigerant, a cooling fin coupled to the refrigerant pipe, and a hydrophilic coating coated on a surface of at least one of the refrigerant pipe and the cooling fin. The hydrophilic coating may contain a first type transition metal oxide that becomes acidic by reacting with moisture formed on the refrigerant pipe or the cooling fin to have antimicrobial activity when the heat exchanger is operated in the cooling operation mode, and a second type transition metal oxide or a post-transition metal oxide that has antimicrobial activity when the heat exchanger is operated in the drying operation mode.

In one embodiment disclosed herein, a transition metal of the first type transition metal oxide may contain at least one selected from a group consisting of tungsten (W), molybdenum (Mo), and zirconium (Zr).

In another embodiment disclosed herein, a transition metal of the second type transition metal oxide may contain at least one selected from a group consisting of zinc (Zn), titanium (Ti), and copper (Cu).

A post-transition metal of the post-transition metal oxide may contain tin (Sn).

The hydrophilic coating may contain one of the second type transition metal oxide and the post-transition metal oxide. In this instance, a total content of the first type transition metal oxide and the second type transition metal oxide or a total content of the first type transition metal oxide and the post-transition metal oxide may be 2 to 10 wt. % of the hydrophilic coating.

The hydrophilic coating may contain both of the second type transition metal oxide and the post-transition metal oxide. In this instance, a total content of the first type transition metal oxide, the second type transition metal oxide, and the post-transition metal oxide may be 2 to 10 wt. % of the hydrophilic coating.

The hydrophilic coating may contain at least one hydrophilic polymer selected from a group consisting of polyvinyl alcohol, polyacrylic acid, polyacetic acid, and polyvinylpyrrolidone.

An average thickness of the hydrophilic coating may be 0.7 to 2 μm.

An average size of the first type transition metal oxide, the second type transition metal oxide, or the post-transition metal oxide may be 0.1 to 10 μm.

Advantageous Effects

According to the present disclosure having the configuration described above, the first type transition metal oxide may perform the antimicrobial and deodorizing activities through the catalytic reaction with moisture during the cooling operation of the heat exchanger. Since the second type transition metal oxide or the post-transition metal oxide performs the antimicrobial activity through the photocatalytic reaction of the heat exchanger, the antimicrobial function can be maintained during the drying operation of the heat exchanger.

Accordingly, the antimicrobial activity can always be provided to the heat exchanger by the hydrophilic coating containing the first type transition metal oxide, the second type transition metal oxide, and the post-transition metal oxide.

In addition, the present disclosure may provide a proper raw material composition of the hydrophilic coating, and provide a thickness of the hydrophilic coating and a size of an inorganic antimicrobial material, thereby maintaining the optimal antimicrobial and odor removal performances of the heat exchanger for a long period of time.

DETAILED DESCRIPTION OF THE DRAWING

MODES FOR CARRYING OUT THE PREFERRED EMBODIMENTS

Hereinafter, a heat exchanger associated with the present disclosure will be described in more detail with reference to the accompanying drawings. Unless clearly indicated otherwise, expressions in a singular number used herein include a plural meaning.

Figure 1:
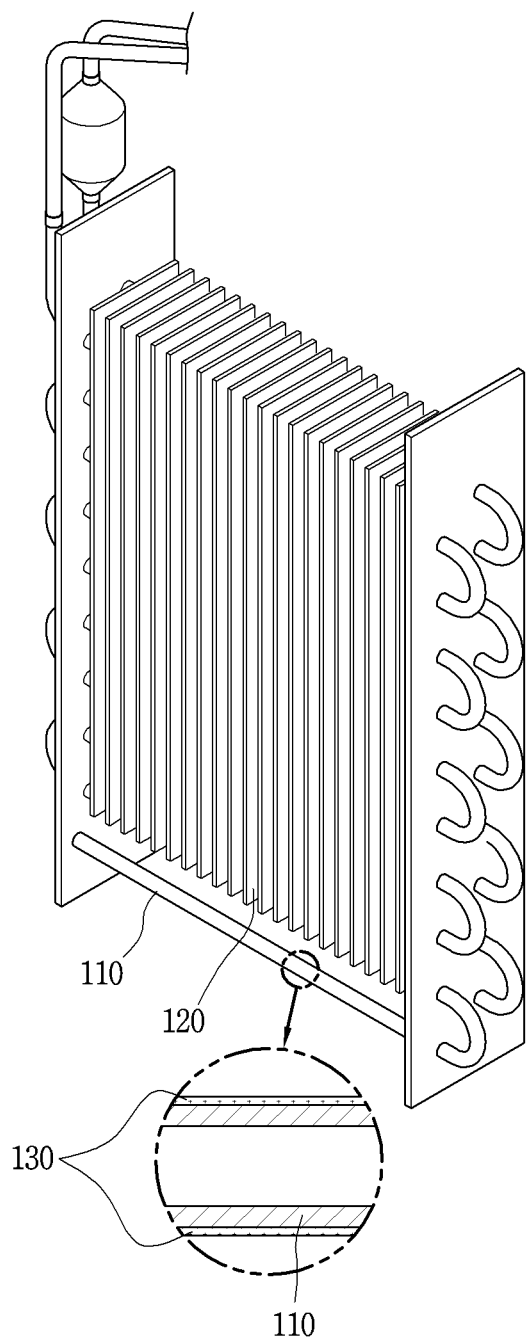
FIG. 1 is a conceptual view showing an example of a heat exchanger provided by the present disclosure.
Figure 2A:
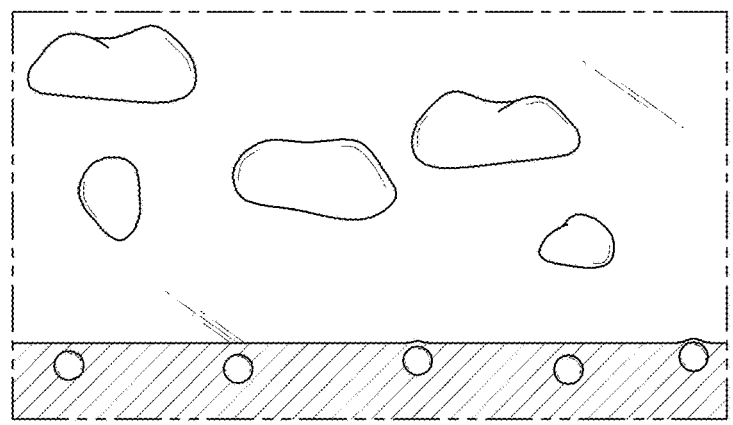
FIGS. 2A to 2E are images showing an antimicrobial mechanism by hydrooxonium ions.
Figure 2B:
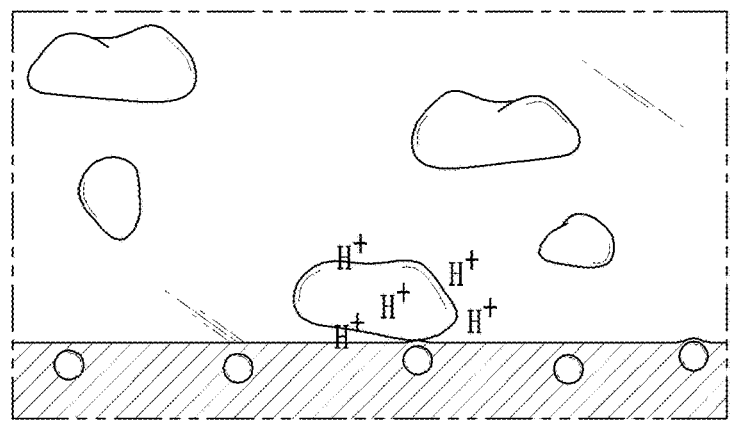
Figure 2C:
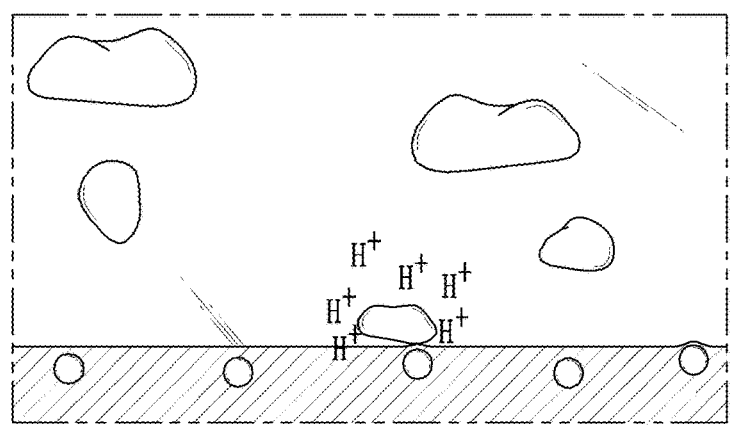
Figure 2D:
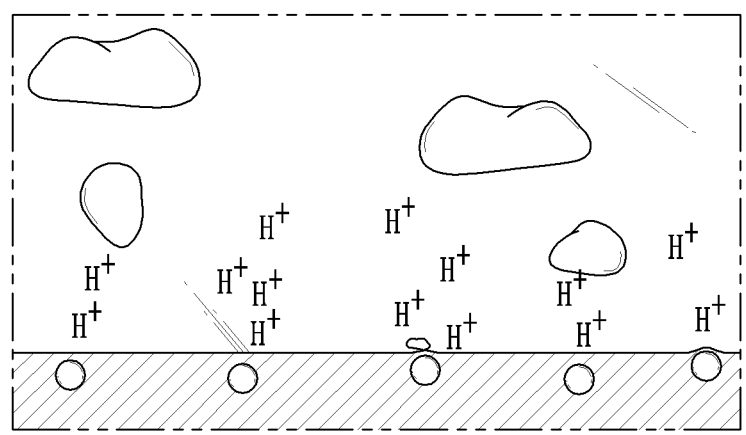
Figure 2E:
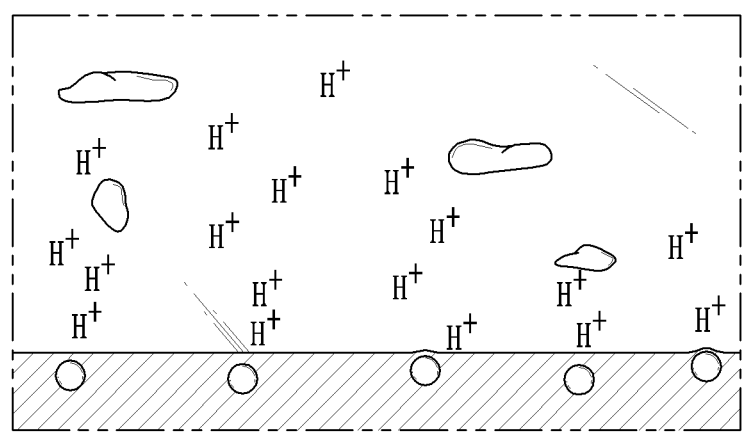

FIG. 1 is a conceptual view showing an example of a heat exchanger provided by the present disclosure.

A refrigerant pipe 110 defines a flow path of a heat exchange fluid. The heat exchange fluid may be, for example, a refrigerant. The refrigerant pipe may be configured to pass through cooling fins in a straight direction, change the direction at an outside of the cooling fins, and repeatedly pass through the cooling fins again.

The cooling fins 120 are provided to improve heat exchange efficiency of the heat exchanger by extending a heat exchange area thereof. The cooling fins are coupled to the refrigerant pipe. Referring to FIG. 1, the cooling fins are defined in the form of a flat plate, and illustrated to be coupled around the refrigerant pipe. The heat exchanger may be provided with a plurality of cooling fins, and respective fins are disposed to be spaced apart from each other.

It may be assumed that the heat exchanger operates as an indoor unit or outdoor unit of an air conditioner. The air conditioner may be operated in various operating modes, such as a cooling operation, a heating operation, a dehumidification operation, and a drying operation.

The cooling operation refers to an operation of cooling a heat exchange target region (a region to be heat-exchanged) of the heat exchanger. In contrast, the heating operation refers to an operation of heating the heat exchange target region of the heat exchanger. The dehumidification operation refers to an operation of reducing an amount of moisture that is present in the heat exchange target region of the heat exchanger so as to lower humidity. The drying operation refers to an operation of receiving wind from a blowing fan provided in the air conditioner to remove condensate formed in the heat exchanger.

When the heat exchanger is operated as an indoor unit or an outdoor unit of the air conditioner, the heat exchanger is operated according to the operation of the air conditioner. For example, when the heat exchanger is operated as an indoor unit of the air conditioner, the heat exchanger cools indoor air through heat exchange between the indoor air and refrigerant during the cooling operation of the air conditioner. On the contrary, when the heat exchanger is operated as an outdoor unit of the air conditioner, the heat exchanger heats outdoor air through heat exchange between the outdoor air and refrigerant during the cooling operation of the air conditioner.

When temperature of the heat exchanger used as the indoor unit becomes lower than a dew point of room temperature, unsaturated air reaches a saturated state to start condensation of water vapor. As a result, condensate is formed on a surface of the heat exchanger.

The formation of condensate does not necessarily occur only during the cooling operation of the air conditioner. When the air conditioner is operated in a heating mode, the outdoor unit cools outdoor air. Furthermore, condensate may be formed on a surface of the heat exchanger used as the outdoor unit. Therefore, the heat exchanger operated in a cooling operation mode is a concept including both the indoor unit of the air conditioner operated in an air cooling mode and the outdoor unit of the air conditioner operated in a heating mode.

Since bacteria such as mold grow in a humid environment, bacteria may easily grow when condensate is formed on the surface of the heat exchanger. As a result, the air conditioner may be operated in a drying operation mode to dry the condensate.

During a drying operation of the air conditioner, a blowing fan provided in the air conditioner generates wind toward the heat exchanger. The heat exchanger receives wind from the blowing fan, and condensate formed on the heat exchanger is dried.

However, the drying process alone is unable to fundamentally prevent bacteria from growing in the heat exchanger. Therefore, the heat exchanger of the present disclosure includes a hydrophilic coating 130 to prevent the growth of bacteria.

The hydrophilic coating 130 is coated on a surface of at least one of the refrigerant pipe and the cooling fin. Since the hydrophilic coating 130 has a hydrophilic property, condensate is easily formed on the hydrophilic coating 130.

The hydrophilic coating 130 contains a hydrophilic polymer that provides hydrophilicity. The hydrophilic polymer may contain at least one selected from a group consisting of polyvinyl alcohol, polyacrylic acid, polyacetic acid, and polyvinylpyrrolidone.

The hydrophilic coating 130 may contain a metallic salt such as metal sulfate. The hydrophilic coating 130 may also contain acid/base chemicals.

The hydrophilic coating 130 contains a first type transition metal oxide to have an antimicrobial activity, and also contains a second type transition metal oxide and/or a post-transition metal oxide. Here, the first type transition metal oxide and the second type transition metal oxide are provided to distinguish from each other, and the term itself does not have any special technical meaning.

The first type transition metal oxide exhibits acidity by reacting with moisture formed on the refrigerant pipe or the cooling fin to have antimicrobial and/or deodorization activities (odor removal performance) during the cooling operation of the heat exchanger. Here, the acidity is a concept including weak acidity (pH 5-6).

The first type transition metal oxide generates an acidic or weakly acidic metallic acid through a catalytic reaction with moisture, and the acidic or weakly acidic metallic acid provides an antimicrobial property to the hydrophilic coating 130.

A transition metal of the first type transition metal oxide may contain at least one selected from a group consisting of tungsten (W), molybdenum (Mo), and zirconium (Zr). Since the first type transition metal oxide contains at least one selected from the above group, it may be made of an alloy.

When the transition metal of the first type transition metal oxide is made of molybdenum, the molybdenum oxide generates hydrooxonium ions (H3O+) through a catalytic reaction with moisture. The catalytic reaction refers to Chemical Formulas 1 and 2 below, and in the case of other transition metals, metal acids are produced through similar chemical formulas.

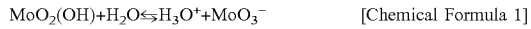

$$MoO_2(OH) + H_2O \leftrightarrows H_3O^+ + MoO_3^-$$ [Chemical Formula 1]

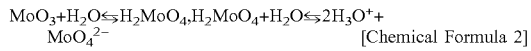

$$MoO_3 + H_2O \leftrightarrows H_2MoO_4, H_2MoO_4 + H_2O \leftrightarrows 2H_3O^+ + MoO_4^{2-}$$ [Chemical Formula 2]

Since hydrooxonium ions exhibit acidic properties, direct contact with a surface of bacteria causes a sterilization activity. Moisture is required for the catalytic reaction between the first type transition metal oxide and the moisture. The reason why the hydrophilic coating 130 has hydrophilicity is to induce the reaction between the first type transition metal oxide and moisture through the formation of condensate.

FIGS. 2A to 2E are images showing an antimicrobial mechanism by hydrooxonium ions.

A hydrophilic coating is depicted at the bottom of each image, and the hydrophilic coating contains a first type transition metal oxide. A size value of the first type transition metal oxide may be larger than an average thickness value of the hydrophilic coating.

As bacteria migrate to the hydrophilic coating, hydrooxonium ions are generated due to the catalytic reaction between moisture and the first type transition metal oxide contained in the hydrophilic coating. The hydrooxonium ions are injected through cell membranes of the bacteria, which destroys the DNA structure of the bacteria by distorting pH-equilibrium at sensitive sites such as cell enzymes and transport systems.

Figure 3:
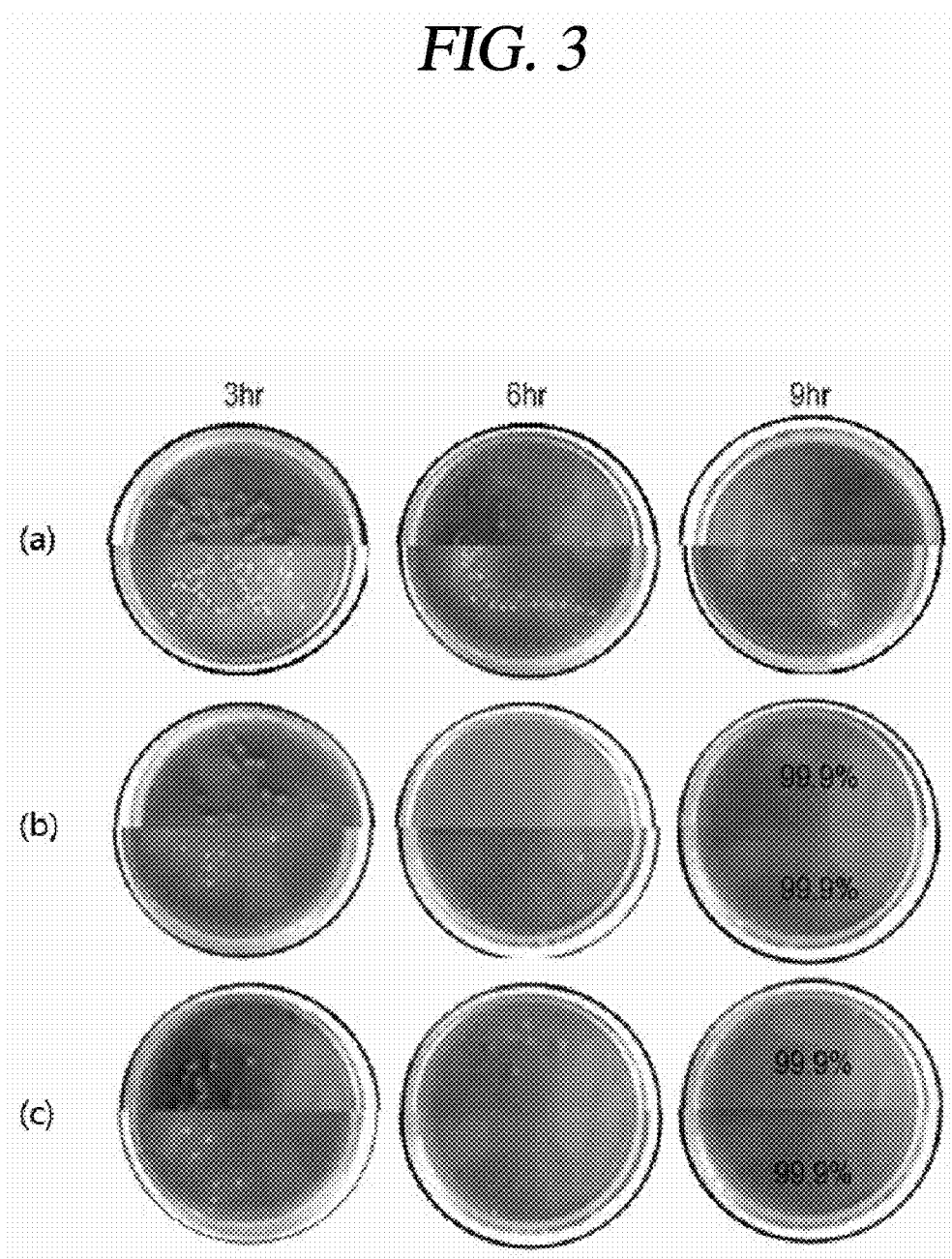
FIG. 3 is an experimental result showing an antimicrobial effect of a first type transition metal oxide compared to a general-purpose hydrophilic coating.

FIG. 3 is an experimental result showing an antimicrobial effect of a first type transition metal oxide compared to a general-purpose hydrophilic coating.

A comparative example is (a) a general-purpose hydrophilic coating that does not contain a first type transition metal oxide. For examples of the present disclosure, (b) adding 3 wt. % of zinc molybdate (ZnMoO4) to the general-purpose hydrophilic coating (Example 1), and (c) adding 3 wt. % of molybdenum/tungsten (Mo/W) mixed oxide to the general-purpose hydrophilic coating (Example 2) were selected.

The experiment used a film adhesion method, and the contact time was set to 3, 6, and 9 hours to verify the antimicrobial performance according to each time. A colon bacterium (*Escherichia coli*) and *Staphylococcus* were selected as bacteria to be tested or experimented (referred to as test bacteria). In each experimental result, an upper semicircle represents an experimental result of *Escherichia coli*, and a lower semicircle represents an experimental result of *Staphylococcus*.

In the case of a general-purpose hydrophilic coating in the comparative example, *Escherichia coli* and staphylococci remain over time. In contrast, in the case of coating of Example 1 and coating of Example 2, *Escherichia coli* and staphylococci were removed over time. In the case of the coating of Example 1 and the coating of Example 2, 99.9% of both *Escherichia coli* and *Staphylococcus* were removed after 9 hours.

Meanwhile, as the first type transition metal oxide generates an acidic or weakly acidic metallic acid through a catalytic reaction with moisture, the acidic or weakly acidic metallic acid provides deodorization activity to the hydrophilic coating 130.

For instance, an amine-based malodorous substance such as trimethylamine {(CH3)3N} is changed to a compound having low odor intensity or an unodorized compound TMAO {TMA N-oxide, (CH3)3NO} through an oxidation reaction as shown in Chemical formula 3.

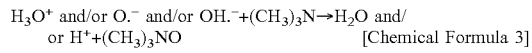

$$H_3O^+ \text{ and/or } O.^- \text{ and/or } OH.^- + (CH_3)_3N \rightarrow H_2O \text{ and/or } H^+ + (CH_3)_3NO$$ [Chemical Formula 3]

As another example, ammonia water (NH3), which is a malodorous substance, may be changed to a form (NH4+) having low odor intensity through a reaction, as shown in Chemical Formula 4, when acidity is increased.

$$H^+ + NH_3 \rightarrow NH_4^+$$ [Chemical Formula 4]

Figure 4:
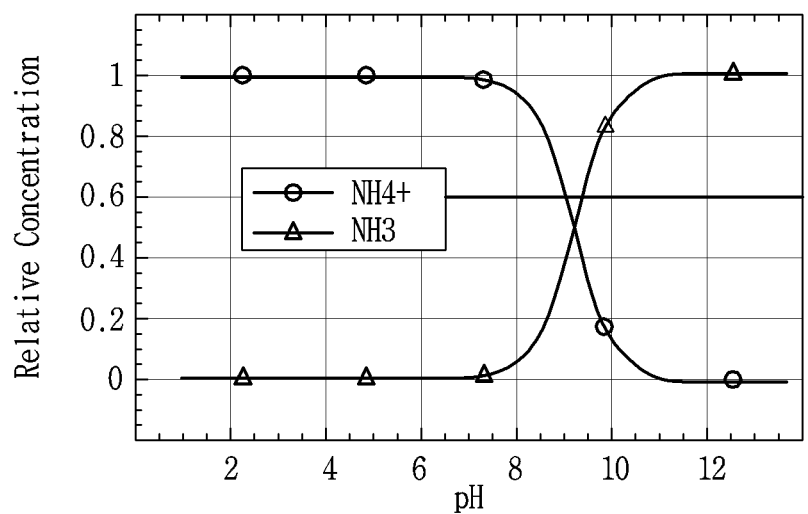
FIG. 4 is a graph showing a change in concentration of $NH_3$ and $NH_4^+$ with pH.

FIG. 4 is a graph showing a change in concentration of NH3 and NH4+ according to pH. A horizontal axis of the graph denotes pH, and a vertical axis of the graph denotes relative concentration. Referring to FIG. 4, as pH is lowered, the relative concentration of NH4+ is increased and conversely the relative concentration of NH3 is lowered. Since NH3 causes worse odors than NH4+, the lowered relative concentration of NH3 may be understood as the first type transition metal oxide has an odor reduction effect.

Figure 5:
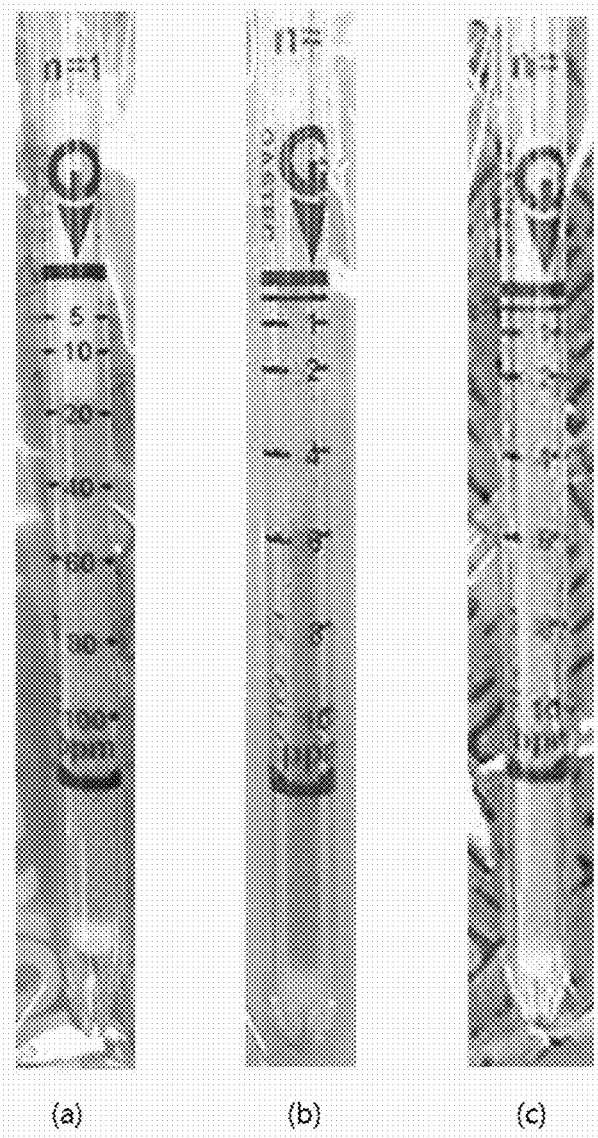
FIG. 5 is a view illustrating a result of exposing trimethylamine in a test solution prepared by adding zinc molybdate ($ZnMoO_4$) to a hydrophilic coating solution.
Figure 6:
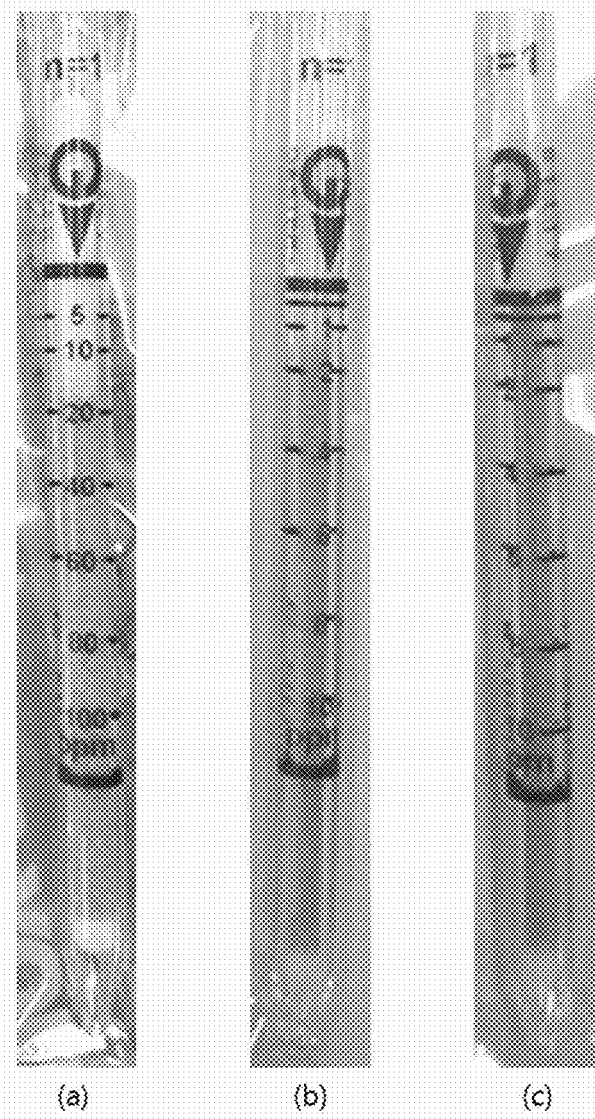
FIG. 6 is a view illustrating a result of exposing trimethylamine in a test solution prepared by adding molybdenum trioxide ($MoO_3$) to a hydrophilic coating solution.
Figure 7:
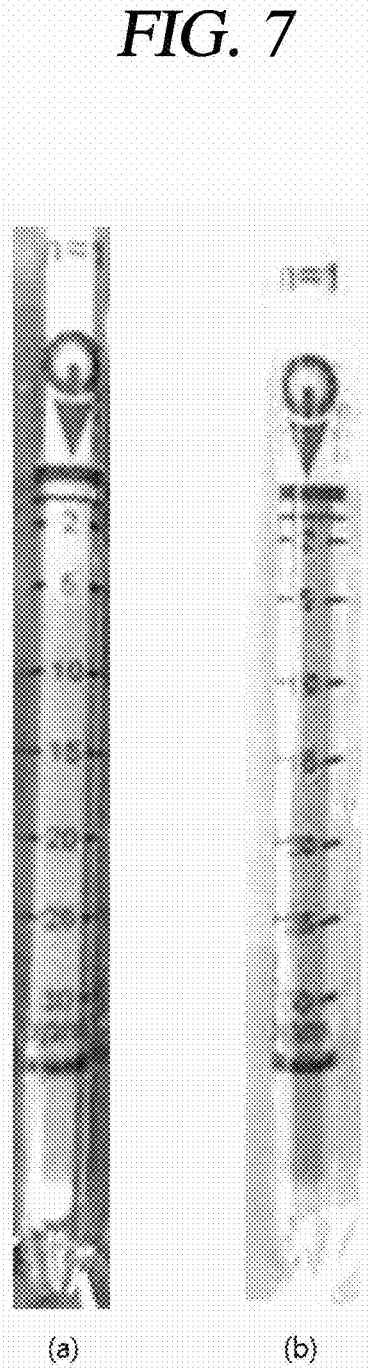
FIG. 7 is a result of exposing ammonia water ($NH_3$) to a test solution prepared by adding molybdenum trioxide ($MoO_3$) to a hydrophilic coating solution.

The odor reduction effect by the first type transition metal oxide can be verified by experimental results of FIGS. 5 to 7.

FIG. 5 is a view illustrating a result of exposing trimethylamine to a test solution prepared by adding zinc molybdate (ZnMoO4) to a hydrophilic coating solution.

In the experiment of FIG. 5, trimethylamine was selected as an odor causing substance. An odor substance to be experimented or tested was prepared by mixing a high concentration of an odor causing substance with water. The prepared odor substance to be experimented or tested was stored at low temperature until before the experiment.

The test solution of FIG. 5 was prepared by adding ZnMoO4 to a hydrophilic coating solution as a reference solution. A mixture was prepared by mixing the prepared test solution with the odor substance to be tested.

The experiment to confirm the odor reduction effect was carried out by a detector tube method. 1 L of nitrogen was introduced into an odor bag, and then only 1.5 mL of the odor substance to be tested was injected into the odor bag. And the mixture was vaporized at 150 for 1 hour. After the vaporization, a detector tube was put in the odor bag, and odor concentration of the gas inside the odor bag was measured. After sampling, added particles were removed using a filter. This same corresponds to (a).

On the other hand, 1 L of nitrogen was introduced into an odor bag, and then only 1.5 mL of the mixture was injected into the odor bag. And the mixture was vaporized at 150 for 1 hour. After the vaporization, a detector tube was put in the odor bag, and odor concentration of the gas in the odor bag was measured. Samples shown in FIG. 5 were taken at different times for which the odor substance to be tested is exposed to the test solution, and the added particles were removed using a filter. These samples correspond to (b) and (c), the exposure time of the sample (b) is 2 minutes, and the exposure time of the sample (c) is 50 minutes.

Odor concentrations of 14 ppm, 2.7 ppm, and 0 ppm were measured from the samples (a), (b), and (c), respectively, by the detector tube method. According to the results, the odor reduction effect of the test solution prepared by adding $ZnMoO_4$ to the hydrophilic coating solution is verified, and it is also verified that the odor concentration is further lowered as the exposure time extends.

FIG. 6 is a view illustrating a result of exposing trimethylamine to a test solution prepared by adding molybdenum trioxide ($MoO_3$) to a hydrophilic coating solution.

The experiment of FIG. 6 is the same as the experiment of FIG. 5 except for a difference in test solution. The test solution was prepared by adding $MoO_3$ to the hydrophilic coating solution as the reference solution.

A sample (a) corresponds to odor concentration of only an odor substance to be tested without the test solution added. Samples (b) and (c) correspond to odor concentrations of a mixture in which the odor substance to be tested and the test solution are mixed with each other. The sample (b) and the sample (c) are different from each other in exposure time. The exposure time of the sample (b) is 2 minutes and the exposure time of the sample (c) is 50 minutes.

Odor concentrations of 14 ppm, 0.8 ppm, and 0 ppm were measured from the samples (a), (b), and (c), respectively, by the detector tube method. According to the results, the odor reduction effect of the test solution prepared by adding $MoO_3$ to the hydrophilic coating solution is verified, and it is also verified that the odor concentration is further lowered as the exposure time extends.

FIG. 7 is a view illustrating a result of exposing ammonia water ($NH_3$) to a test solution prepared by adding molybdenum trioxide ($MoO_3$) to a hydrophilic coating solution.

The experiment of FIG. 7 is the same as the experiment of FIG. 6 excluding that an odor causing substance is ammonia water ($NH_3$). On the other hand, similar to the experiment of FIG. 6, a test solution was prepared by adding $MoO_3$ to the hydrophilic coating solution as the reference solution.

A sample (a) corresponds to odor concentration of only the odor substance to be tested without the test solution added. A sample (b) corresponds to odor concentration of a mixture in which the odor substance to be tested and the test solution are mixed with each other.

Odor concentrations of 6 ppm and 0 ppm were measured from the samples (a) and (b), respectively, by the detector tube method. From this result, the odor reduction effect of the test solution prepared by adding $MoO_3$ to the hydrophilic coating solution is verified.

Hereinafter, a second type transition metal oxide and a post-transition metal oxide will be described.

The second type transition metal oxide and the post-transition metal oxide have antimicrobial activities during a drying operation. After the cooling operation of the heat exchanger, a drying operation for drying condensate is started. Since the heat exchanger receives wind from the blowing fan during the drying operation, the condensate is dried from the surface of the heat exchanger. Accordingly, a catalytic reaction between the first type transition metal oxide and moisture does not occur, and surfaces of a refrigerant pipe and a cooling fin are changed to be neutral or basic.

Unlike the first type transition metal oxide, which causes an antimicrobial action through a catalytic reaction with moisture, at least part of the second type transition metal oxide and the post-transition metal oxide may act as a photocatalyst.

The photocatalyst acts as a catalyst by receiving light. When light is irradiated on the photocatalyst, electrons and holes are generated. The electrons react with oxygen on a surface of the photocatalyst to produce superoxide anions ($O_2-$), and the holes react with moisture in the air to produce hydroxyl radicals (OH). Since the hydroxyl radicals have excellent oxidative degradation with respect to organic substances, they decompose bacteria into water and carbon dioxide. For this reason, the photocatalyst provide an antimicrobial function.

In addition, bacteria cause odors. If the bacteria are decomposed into water and carbon dioxide which are odorless substances, the odors caused by bacteria can be removed.

A transition metal of the second type transition metal oxide may contain at least one selected from a group consisting of zinc (Zn), titanium (Ti), and copper (Cu). A transition metal of the post-transition metal oxide may contain tin (Sn).

The production of the hydroxyl radicals requires moisture, but only moisture in the air is sufficient. The catalytic reaction of the photocatalyst only requires light, not moisture. Light existing in nature is sufficient to cause the catalytic reaction of the photocatalyst. Therefore, the photocatalyst can cause the antimicrobial function during the drying operation of the heat exchanger.

An average thickness of the hydrophilic coating may be 0.7 to 2 μm. An average size of the first type transition metal oxide, the second type transition metal oxide, and the post-transition metal oxide may be 0.1 to 10 μm. Roughness exists on the surface of the hydrophilic coating when the average size value of the first type transition metal oxide, the second type transition metal oxide, and the post-transition metal oxide is greater than the average thickness value of the hydrophilic coating. This results from irregular shapes of the first type transition metal oxide, the second type transition metal oxide, and the post-transition metal oxide. This roughness may form a natural drainage structure of moisture on the surface of the hydrophilic coating.

The hydrophilic coating may contain only one or both of the second type transition metal oxide and the post-transition metal oxide.

When the hydrophilic coating contains only one of the second type transition metal oxide and the post-transition metal oxide, a total content of the first type transition metal oxide and the second type transition metal oxide is 2 to 10 wt. % (percent by weight) of the hydrophilic coating. Or a total content of the first type transition metal oxide and the post-transition metal oxide is 2 to 10 wt. % (percent by weight) of the hydrophilic coating.

When the hydrophilic coating contains both the second type transition metal oxide and the post-transition metal oxide, a total content of the first type transition metal oxide, the second type transition metal oxide and the post-transition metal oxide is 2 to 10 wt. % of the hydrophilic coating.

If the lower limit of the content is lower than 2 wt. %, a reaction rate for an antimicrobial action is slow, which causes a difficulty in a rapid antimicrobial action. On the contrary, if the upper limit of the content exceeds 10 wt. %, the antimicrobial effect is saturated.

Silver (Ag) is known to have strong antimicrobial activity, but it has a disadvantage of high cost and lacks mechanical properties such as elasticity, bending, ductility, and the like. On the other hand, the transition metal oxides and post-transition metal oxides have not only low-cost advantages but also mechanical properties which are not obtained from silver. Furthermore, the transition metal oxides and post-transition metal oxides are stable against contamination by proteins and sugar components. In addition, the transition metal oxides and post-transition metal oxides have long-term stability because they have low water solubility of 0.003 mol/L or less.

Hereinafter, a method of forming a hydrophilic coating will be described.

In order to form a hydrophilic coating, an inorganic antimicrobial substance is first added to a hydrophilic coating solution to form a hybrid antimicrobial hydrophilic coating solution mixture. The coating solution mixture is coated on at least one of a refrigerant tube and a cooling fin and cured to form a hydrophilic coating.

The hydrophilic coating solution is 89 to 98 wt. % of water and dihydrogen oxide, 0.1 to 10 wt. % of hydrophilic polymer, 0.1 to 1 wt. % of metallic salt, and 0.1 to 3 wt. % of acid and base chemicals. The hydrophilic polymer and the metal salt have been described above. The hydrophilic coating formed by the hydrophilic coating solution contains C, H, O, N, S, P, F, Na, Ca, Si, and the like.

An inorganic antimicrobial material contains a first type transition metal oxide, a second type transition metal oxide, and a post-transition metal oxide. Finally, the inorganic antimicrobial material is contained by 2 to 10 wt. % of the hydrophilic coating deposited on the refrigerant pipe or the cooling fin, based on a weight ratio.

The heat exchanger described above may not be limited to the configuration and method of the foregoing embodiments, but all or part of those embodiments can be selectively combined to make various modifications.

INDUSTRIAL AVAILABILITY

The present disclosure can be applied to a technical field related to heat exchangers.

The invention claimed is:

1. A heat exchanger operated in a cooling operation mode for cooling a region to be heat-exchanged or in a drying operation mode for receiving wind supplied from a blowing fan, the heat exchanger comprising:
 a refrigerant pipe that defines a flow path of a refrigerant;
 a cooling fin coupled to the refrigerant pipe; and
 a hydrophilic coating coated on a surface of at least one of the refrigerant pipe or the cooling fin, wherein the hydrophilic coating contains:
  a first type transition metal oxide that becomes acidic by reacting with moisture formed on the refrigerant pipe or the cooling fin to have antimicrobial activity when the heat exchanger is operated in the cooling operation mode; and
  a second type transition metal oxide or a post-transition metal oxide that has antimicrobial activity when the heat exchanger is operated in the drying operation mode, wherein the first type transition metal oxide exhibits acidity by a catalytic reaction with moisture formed on the refrigerant pipe or the cooling fin to have antimicrobial activity when the heat exchanger is operated in the cooling operation mode, wherein the second type transition metal oxide or the post-transition metal oxide performs antimicrobial activity through a photocatalytic reaction of the heat exchanger when the heat exchanger is operated in the drying operation mode, wherein a total content of the first type transition metal oxide and the second type transition metal oxide or a total content of the first type transition metal oxide and the post-transition metal oxide is 2 to 10 wt. % of the hydrophilic coating, wherein the first type transition metal oxide exhibits weak acidity by the catalytic reaction with moisture formed on the refrigerant pipe or the cooling fin, and wherein a pH value of the weak acidity is in a range of 5 pH to 6 pH.

2. The heat exchanger of claim 1, wherein a transition metal of the first type transition metal oxide contains at least one selected from a group consisting of tungsten (W), molybdenum (Mo), and zirconium (Zr).

3. The heat exchanger of claim 1, wherein a transition metal of the second type transition metal oxide contains at least one selected from a group consisting of zinc (Zn), titanium (Ti), and copper (Cu), and a post-transition metal of the post-transition metal oxide contains tin (Sn).

4. The heat exchanger of claim 1, wherein the hydrophilic coating contains both the second type transition metal oxide and the post-transition metal oxide.

5. The heat exchanger of claim 1, wherein a total content of the first type transition metal oxide, the second type transition metal oxide, and the post-transition metal oxide is 2 to 10 wt. % of the hydrophilic coating.

6. The heat exchanger of claim 1, wherein the hydrophilic coating contains at least one hydrophilic polymer selected from a group consisting of polyvinyl alcohol, polyacrylic acid, polyacetic acid, and polyvinylpyrrolidone.

7. The heat exchanger of claim 1, wherein an average thickness of the hydrophilic coating is 0.7 to 2 µm.

8. The heat exchanger of claim 1, wherein an average size of the first type transition metal oxide, the second type transition metal oxide, or the post-transition metal oxide is 0.1 to 10 µm.

9. The heat exchanger of claim 2, wherein the transition metal of the first type transition metal oxide is an alloy.

10. A heat exchanger operated in a cooling operation mode for cooling a region to be heat-exchanged or in a drying operation mode for receiving wind supplied from a blowing fan, the heat exchanger comprising:
 a refrigerant pipe that defines a flow path of a refrigerant;
 a cooling fin coupled to the refrigerant pipe; and
 a hydrophilic coating coated on a surface of at least one of the refrigerant pipe or the cooling fin, wherein the hydrophilic coating contains:
  a first type transition metal oxide that becomes acidic by reacting with moisture formed on the refrigerant pipe or the cooling fin to have antimicrobial activity when the heat exchanger is operated in the cooling operation mode; and
  a second type transition metal oxide or a post-transition metal oxide that has antimicrobial activity when the heat exchanger is operated in the drying operation mode, wherein the first type transition metal oxide exhibits acidity by a catalytic reaction with moisture formed on the refrigerant pipe or the cooling fin to have antimicrobial activity when the heat exchanger is operated in the cooling operation mode, wherein the second type transition metal oxide or the post-transition metal oxide performs antimicrobial activity through a photocatalytic reaction of the heat exchanger when the heat exchanger is operated in the drying operation mode, wherein a total content of the first type transition metal oxide and the second type transition metal oxide or a total content of the first type transition metal oxide and the post-transition metal oxide is 2 to 10 wt. % of the hydrophilic coating, wherein the hydrophilic coating contains at least one hydrophilic polymer selected from a group consisting of polyvinyl alcohol, polyacrylic acid, polyacetic acid, and polyvinylpyrrolidone, and wherein the hydrophilic coating contains 89 to 98 wt. % of water, 0.1 to 10 wt. % of the hydrophilic polymer, 0.1 to 1 wt. % of a metallic salt, and 0.1 to 3 wt. % of acid and base chemicals.

11. The heat exchanger of claim 10, wherein the metallic salt contains metal sulfate.

\* \* \* \* \*